(12) United States Patent
De Kock et al.

(10) Patent No.: US 8,119,801 B2
(45) Date of Patent: Feb. 21, 2012

(54) HIV INHIBITING 2-(4-CYANOPHENYL)-6-HYDROXYLAMINOPYRIMIDINES

(75) Inventors: Herman Augustinus De Kock, Arendonk (BE); Piet Tom Bert Paul Wigerinck, Terhagen (BE)

(73) Assignee: Tibotec Pharmaceuticals Ltd., Little Island (IE)

( * ) Notice: Subject to any disclaimer, the term of this patent is extended or adjusted under 35 U.S.C. 154(b) by 211 days.

(21) Appl. No.: 12/690,673

(22) Filed: Jan. 20, 2010

(65) Prior Publication Data

US 2010/0121060 A1 May 13, 2010

Related U.S. Application Data

(63) Continuation of application No. 11/814,982, filed as application No. PCT/EP2006/060407 on Mar. 2, 2006, now abandoned.

(30) Foreign Application Priority Data

Mar. 4, 2005 (EP) .................................... 05101707

(51) Int. Cl.
*C07D 239/48* (2006.01)
(52) U.S. Cl. ...................................................... 544/321
(58) Field of Classification Search .................... 544/321
See application file for complete search history.

(56) References Cited

U.S. PATENT DOCUMENTS 3,459,731 A    8/1969   Gramera et al.

FOREIGN PATENT DOCUMENTS

| WO | WO 97/18839 A1 | 5/1997 |
| WO | WO 00/27825 A1 | 5/2000 |

OTHER PUBLICATIONS

Ludovici et al., "Evolution of Anti-HIV Drug Candidates. Part 3: Diarylpyrimidine (DAPY) Analogues", Bioorganic & Medicinal Chemistry Letters, vol. 11, pp. 2235-2239 (2001).
International Search Report dated May 3, 2006 for related International Application No. PCT/EP2006/060407.

*Primary Examiner* — Deepak Rao

(57) ABSTRACT

HIV replication inhibitors of formula

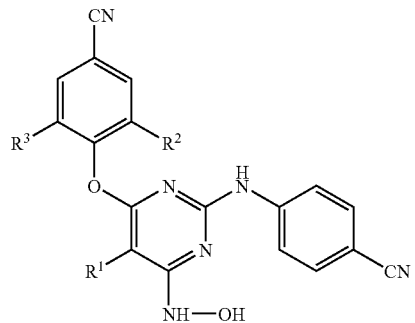

pharmaceutically acceptable addition salts; or stereochemically isomeric forms thereof, wherein $R^1$ is halo; $R^2$ and $R^3$ each independently are $C_{1-6}$alkyl; pharmaceutical compositions containing these compounds as active ingredient and processes for preparing these compounds and compositions.

1 Claim, No Drawings

HIV INHIBITING 2-(4-CYANOPHENYL)-6-HYDROXYLAMINOPYRIMIDINES

CROSS REFERENCE TO RELATED APPLICATIONS

This application is a continuation of U.S. Ser. No. 11/814,982, filed Jul. 27, 2007, now abandoned which was in turn a national stage application Patent Application No. PCT/EP2006/060407, filed Mar. 2, 2006, which application claims priority from EPO Patent Application No. 05101707.7, filed Mar. 4, 2005, both of which are hereby incorporated by reference in their entirety.

The present invention concerns 2-(4-cyanophenyl)-6-hydroxylaminopyrimidines having HIV (Human Immunodeficiency Virus) replication inhibiting properties. The invention further relates to methods for the preparation of these pyrimidines and pharmaceutical compositions comprising these compounds and the use thereof in the prevention or the treatment of HIV infection.

Resistance of the HIV virus against currently available HIV drugs continues to be a major cause of therapy failure. This has led to the introduction of combination therapy of two or more anti-HIV agents usually having a different activity profile. Significant progress was made by the introduction of HAART therapy (Highly Active Anti-Retroviral Therapy), which has resulted in an important reduction of morbidity and mortality in HIV patient populations treated therewith. HAART involves various combinations of nucleoside reverse transcriptase inhibitors (NRTIs), non-nucleoside reverse transcriptase inhibitors (NNRTIs) and protease inhibitors (PIs). Current guidelines for antiretroviral therapy recommend such triple combination therapy regimen even for initial treatment. However, these multidrug therapies not always are effective and never completely eliminate HIV. It has been reported that half of the patients receiving anti-HIV combination therapy do not respond fully to the treatment, mainly because of resistance of the virus to one or more drugs used. Switching to alternative combinations usually provides temporary relief but any form of long-term treatment will fail at the end because of the development of multidrug resistance. Moreover, it has been shown that resistant virus is carried over to newly infected individuals, resulting in severely limited therapy options for these drug-naive patients.

The targeted enzymes in the HIV virus are able to mutate in such a way, that the known drugs become less effective, or even ineffective against these mutant HIV viruses. Or, in other words, the HIV virus creates an ever-increasing resistance against the available drugs. More and more of the HIV strains resistant to NNRTIs found in patients that do not respond to anti-HIV therapy are double or even multi-mutated strains. Such HIV mutant strains bear two or more mutations at the reverse transcriptase gene and therefore show strong resistance towards NNRTI based therapy.

Because of its ability to quickly mutate and to create resistance towards existing drug therapies, there is a continued need for new combinations of active ingredients that are effective against HIV. In particular, there is a continued need for new types of anti-HIV effective active ingredients, differing in chemical structure and activity profile for use in new types of combination therapy. There is a specific need for new types of anti-HIV effective active ingredients that are active against double and multiple mutated HIV strains. Finding such active ingredients therefore is a highly desirable goal to achieve.

The present invention provides a particular novel series of bisaryl substituted pyrimidine derivatives which may find use in HIV therapy, in particular as a new component of drug combinations. Bisaryl substituted pyrimidines having HIV replication inhibiting properties are known from WO00/27825.

The novel series of pyrimidine derivatives of the present invention behave superior in terms of HIV replication inhibiting properties, in particular against HIV strains having double or multiple mutations at the reverse transcriptase gene.

The present invention concerns a compound of formula

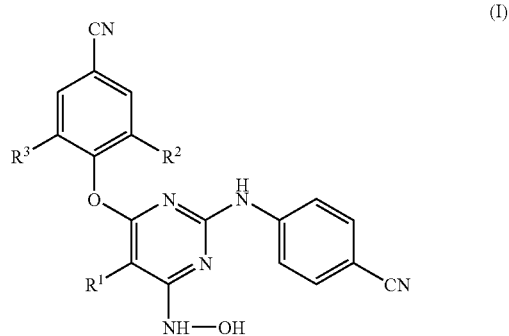

(I)

the pharmaceutically acceptable addition salts; or stereochemically isomeric form thereof, wherein
$R^1$ is halo;
$R^2$ and $R^3$ each independently are $C_{1-6}$alkyl.

As used herein the term "$C_{1-4}$alkyl" defines straight or branched chain saturated hydrocarbon radicals having from 1 to 4 carbon atoms such as methyl, ethyl, 1-propyl, 2-propyl, 1-butyl, 2-butyl, 2-methyl-1-propyl, and the like; "$C_{1-6}$alkyl" encompasses $C_{1-4}$alkyl radicals and the higher homologues thereof having 5 or 6 carbon atoms such as 1-pentyl, 2-pentyl, 3-pentyl, 1-hexyl, 2-hexyl, 2-methyl-1-butyl, 2-methyl-1-pentyl and the like. Of interest amongst $C_{1-6}$alkyl are the $C_{1-4}$alkyl radicals.

The term halo encompasses fluoro, chloro, bromo and iodo.

For therapeutic use, salts of the compounds of formula (I) are those wherein the counter ion is pharmaceutically acceptable. However, salts of acids and bases, which are non-pharmaceutically acceptable may also find use, for example, in the preparation or purification of a pharmaceutically acceptable compound. All salts, whether pharmaceutically acceptable or not are included within the ambit of the present invention.

The term "pharmaceutically acceptable addition salts" as used herein is meant to comprise the therapeutically active non-toxic acid addition salt forms, which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The compounds of formula (I) containing acidic protons may be converted into their therapeutically active non-toxic metal or amine addition salt forms by treatment with appropriate organic and inorganic bases.

The term addition salt also comprises the hydrates and solvent addition forms which the compounds of formula (I) are able to form. Examples of such forms are e.g. hydrates, alcoholates and the like.

Some of the compounds of formula (I) and their addition salts may contain one or more centers of chirality and exist as stereochemically isomeric forms. Stereoiosomers may exist where $R^2$ and $R^3$ are $C_{4-6}$alkyl. The term "stereochemically isomeric forms" as used herein defines all the possible stereoisomeric forms which the compounds of formula (I), and their addition salts may possess. Stereochemically isomeric forms of the compounds of formula (I) are intended to be embraced within the scope of this invention.

Preferred subgroups of compounds are those compounds of formula (I) as specified above, or any subgroup of compounds of formula (I) specified herein, wherein $R^1$ is chloro or bromo, more preferably wherein $R^1$ is bromo.

Other preferred subgroups of compounds are those compounds of formula (I) as specified above, or any subgroup of compounds of formula (I) specified herein, wherein $R^2$ and $R^3$ are $C_{1-4}$alkyl, more preferably wherein $R^2$ and $R^3$ are methyl.

Of particular interest are those compounds wherein $R^1$ is bromo, $R^2$ and $R^3$ are methyl; or wherein $R^1$ is chloro, and $R^2$ and $R^3$ are methyl.

In general, the compounds of formula (I) can be prepared by reacting a pyrimidine derivative of formula (III) with a protected hydroxylamine of formula $NH_2OP$, thus obtaining an intermediate (II) from which the protecting group is removed afterwards. The group W in the pyrimidine derivatives of formula (III), represents a suitable leaving group such as halo, e.g. chloro or bromo, preferably it is chloro.

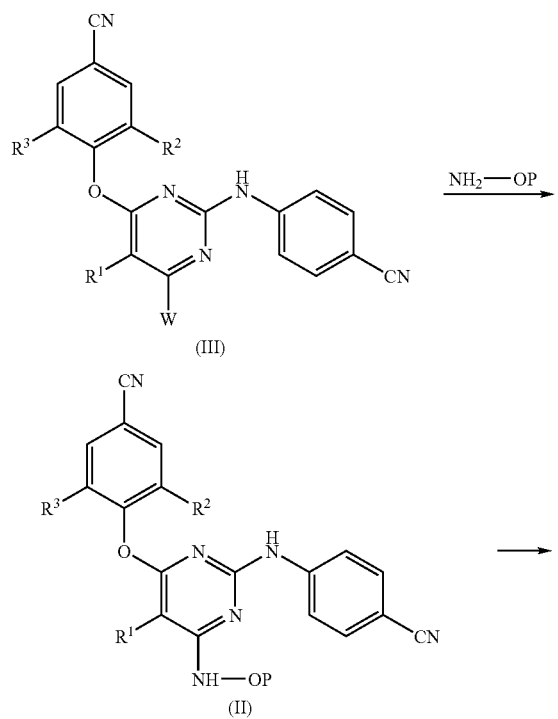

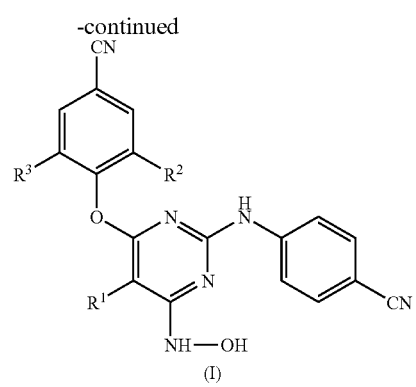

(I)

In an alternative embodiment, intermediate (III) may be reacted with hydroxylamine to directly prepare the compounds of formula (I) as in the following reaction scheme:

Suitable protecting groups (represented by P in the above scheme) include any of the hydroxy-protecting groups used in the art including those which can be removed by acidic cleavage such as methoxyethoxymethyl (MEM), tetrahydropyranyl (THP), tertiary butyl (t.Bu) and the like, or by hydrogenation such as benzyl (Bz) and the like, trialkyl silyl groups such as trimethylsilyl (TMS), t.butyldimethylsilyl (TBDMS), triisopropylsilyl (TIPS), t.butyldiphenylsilyl, and the like, which may be cleaved under acidic or basic conditions. Preferred is the THP group.

The reaction of starting material (III) with the protected hydroxylamine $NH_2OP$ can be carried out in a suitable solvent, preferably in the presence of a base which may be added to pick up the acid that is liberated during the course of the reaction, e.g. an alkali metal carbonate or hydrogencarbonate such as potassium carbonate or organic bases such as the trialkylamines, e.g. triethylamine. Suitable solvents include, for example, acetonitrile, alcohols, e.g. ethanol, 2-propanol; polar aprotic solvents such as N,N-dimethylformamide; N,N-dimethylacetamide, 1-methyl-2-pyrrolidinone, acetonitrile; ethers such as 1,4-dioxane, propylene glycol monomethylether, tetrahydrofuran. Preferred are the ethers, in particular tetrahydrofuran.

The group P in the thus obtained intermediate (II) can be removed following art-known procedures. In case of P being THP, it can be conveniently removed under acidic conditions such as with hydrohalic acids such as hydrochloric acid, with sulfonic acids but also with acidic resins such as sulfon group containing ion exchange resins.

The compounds (I) can also be prepared directly from (III) using hydroxylamine. This reaction can be conducted using similar conditions as that of (III) with protected hydroxylamine.

In the above described synthesis procedures for the preparation of compounds of formula (I) and also in the following procedures for the preparation of intermediates, the radical $R^1$ is halo but it may also represent a precursor of a halo group such as hydroxy or a protected hydroxy (e.g. benzyloxy) which can be converted into a halo group with a halogenating agent such as $POCl_3$ or $POBr_3$. This may be done to avoid undesired side reactions.

The intermediates of formula (II) can also be prepared by reacting an intermediate of formula (IV) or (VI) with an intermediate of formula (V) or (VII), as outlined in the following reaction scheme, wherein $R^1$, $R^2$ and $R^3$ are as specified for the compounds of formula (I) or any subgroup thereof and W represents a suitable leaving group, such as for example halogen, e.g. chloro, bromo and the like. The intermediates of formula (II) can be converted to the end products of formula (I) by a deprotection reaction. Alternatively, intermediates (IV) or (VI) can be used in which the hydroxylamino group is unprotected so that compounds (I) are obtained directly.

The reaction of the pyrimidine derivative (IV) respectively (VI) with the cyanoaniline (V) respectively with the cyanophenyl derivative (VII) is preferably conducted in a suitable solvent, such as for example acetonitrile, an alcohol, such as for example ethanol, 2-propanol; N,N-dimethylformamide; N,N-dimethylacetamide, 1-methyl-2-pyrrolidinone; an ether such as 1,4-dioxane, propylene glycol monomethylether, acetonitrile. The reactions may be done under acid conditions which may be obtained by adding amounts of a suitable acid, e.g. camphor sulfonic acid, and a suitable solvent, such as for example tetrahydrofuran or an alcohol, e.g. ethanol, 1- or 2-propanol, or by using acidified solvents, e.g. hydrochloric acid dissolved in an alkanol such as ethanol, 1- or 2-propanol.

In an alternative embodiment, the unprotected pyrimidine derivatives (IV), i.e. the intermediates (IV) wherein P is hydrogen, may be reacted with (V) thus yielding directly the end products of formula (I). To avoid side reactions, it is preferred to use the protected intermediates (IV) and to remove the group P afterwards.

The intermediates of formula (II) can also be prepared by reacting a cyanophenyl derivative (VIII) with a pyrimidine derivative (IX) or by reacting a cyanophenyl derivative (X) with a pyrimidine derivative (XI) as outlined in the following schemes.

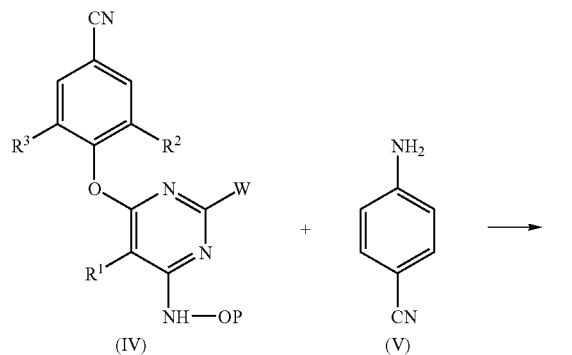

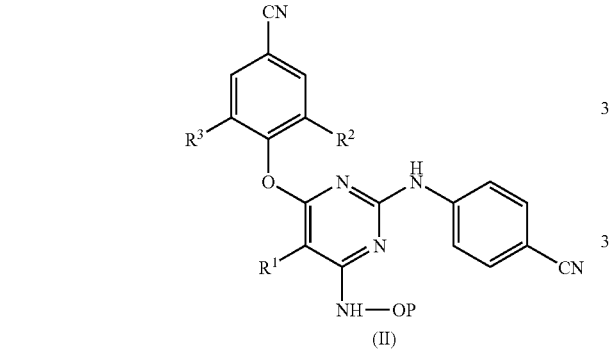

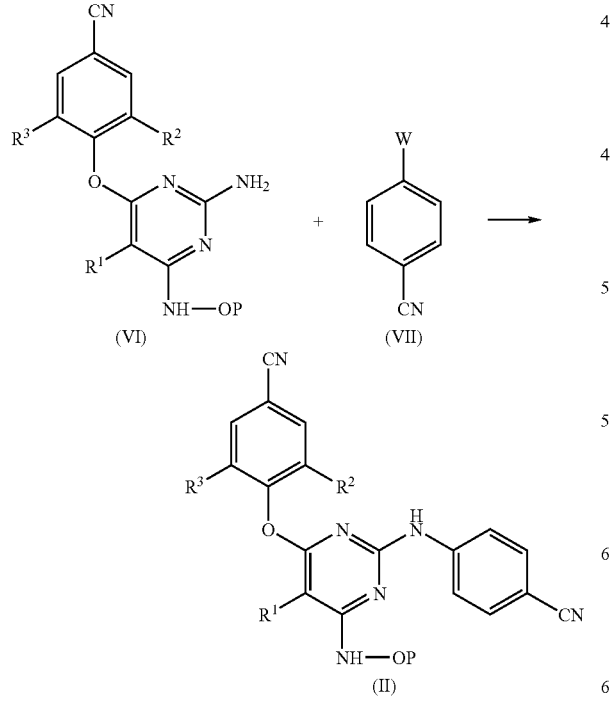

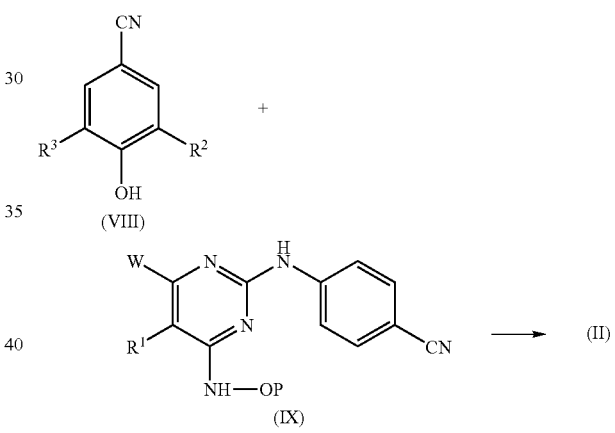

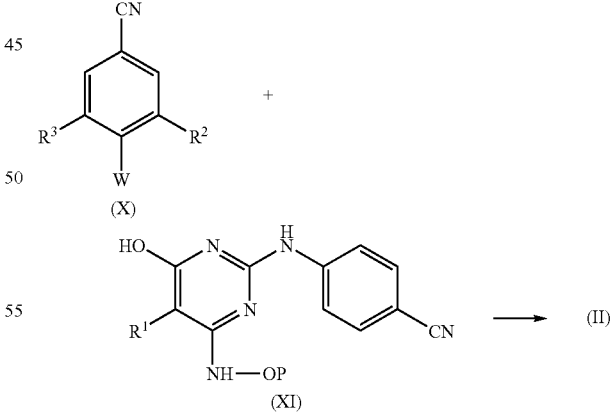

In these reaction schemes $R^1$, $R^2$ and $R^3$ are as specified for the compounds of formula (I) or any subgroup thereof, P is a protecting group as specified above and W represents a suitable leaving group as specified above. These reactions preferably are conducted in a suitable solvent, in particular any of the solvents mentioned above in relation to the reaction of (IV) with (V).

In an alternative embodiment, the unprotected pyrimidine derivatives (IX) or (XI), i.e. the intermediates (IX) or (XI) wherein P is hydrogen, may be reacted with (VIII) or (X) thus yielding directly the end products of formula (I). To avoid side reactions, it is preferred to use the protected intermediates (IX) or (XI) and to remove the group P afterwards.

The compounds of formula (I) may further be prepared by converting compounds of formula (I) into each other according to art-known group transformation reactions. For example the chloro analogs can be converted to the corresponding bromo analogs, or vice versa, by a halogen exchange reaction.

Some of the compounds of formula (I) and some of the precursor intermediates thereof may contain an asymmetric atom. Pure stereochemically isomeric forms of said compounds and said intermediates can be obtained by the application of art-known procedures.

The synthesis of some intermediates used in the previous reaction schemes is described hereinafter wherein in the reaction schemes $R^1$, $R^2$ and $R^3$ are as specified for the compounds of formula (I) or any subgroup thereof and W represents a suitable leaving group, in particular chloro or bromo.

The starting materials of formula (III) can be prepared as described in WO-00/27825. In particular they can be prepared as outlined in the following scheme.

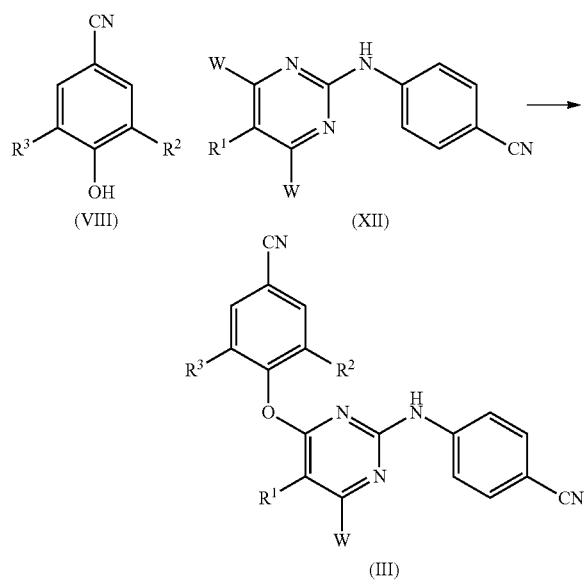

The substituted 4-cyanophenol (VIII) is reacted with pyrimidine derivative (XII), wherein each W independently represents a leaving group such as specified above.

Intermediates of formula (IV) can be prepared as outlined in the following reaction scheme

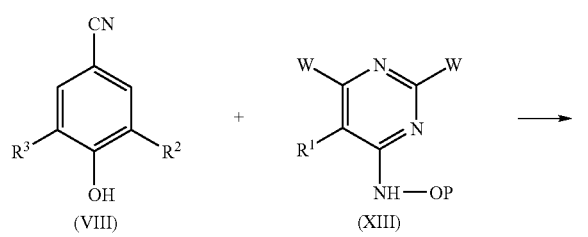

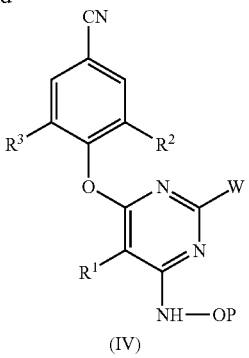

In a similar manner, intermediates (VI) can be prepared starting from a pyrimidine (XIV) as outlined in the following scheme:

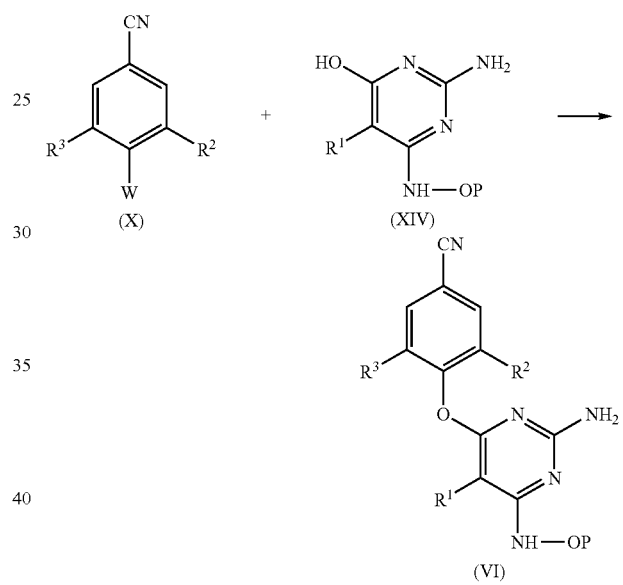

In the above reaction the amino group may or may not be protected by a suitable protective group. In alternative embodiments, the unprotected pyrimidine derivatives (XIII) or (XIV), i.e. the intermediates (XIII) or (XIV) wherein P is hydrogen, may be reacted with (VIII) or (X). To avoid side reactions, it is preferred to use the protected intermediates (XIII) or (XIV) and to remove the group P afterwards.

Intermediates (IX) can be prepared by condensing a pyrimidine derivative (XIII) with a cyanoaniline (V) as outlined in the following scheme. If desired to avoid side reactions, the W-group that is not reacting and/or $R^1$ may be a precursor of halo as set forth above.

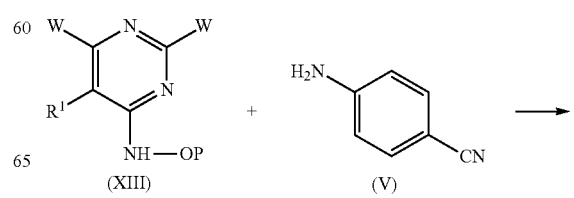

-continued

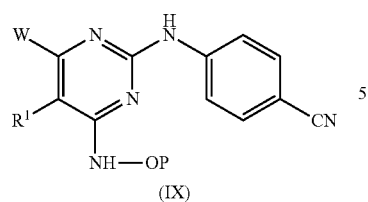
(IX)

Intermediates (XI) can be prepared by condensing a pyrimidine derivative (XV) with a cyanoaniline (V) as outlined in the following scheme. If desired to avoid side reactions, the hydroxy-group in (XV) may be protected and $R^1$ may be a precursor of halo as set forthabove.

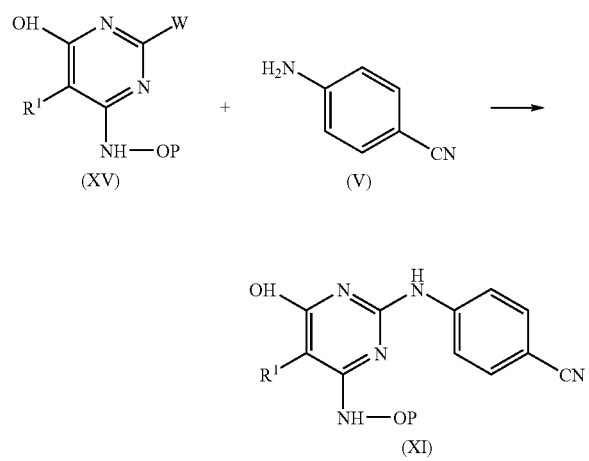

In a further aspect, this invention provides a chemical compound of formula

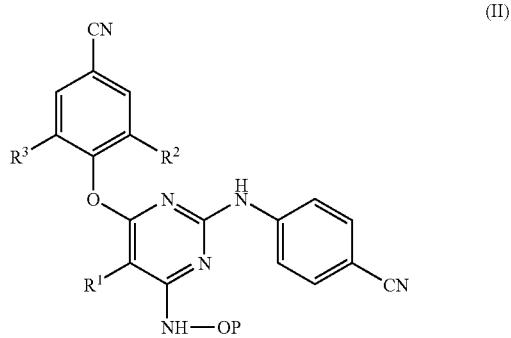
(II)

or an acid-addition salt thereof; or a stereochemically isomeric form thereof, wherein $R^1$, $R^2$ and $R^3$ are as defined in this specification and claims and P is a hydroxy-protecting group. Preferred acid addition salts are the pharmaceutically acceptable acid-addition salts, in particular those mentioned hereinabove. The protecting group P may be as specified above.

In still a further aspect, this invention provides a chemical compound of formula (III) wherein W is chloro, $R^1$ is bromo and $R^2$ and $R^3$ are methyl, which compound can be represented by formula (III-a):

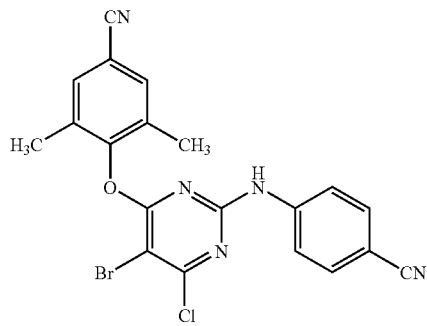
(III-a)

or an acid-addition salt thereof. Preferred acid addition salts are the pharmaceutically acceptable acid-addition salts, in particular those mentioned hereinabove.

The compounds of formula (I) show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever-decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), the pharmaceutically acceptable addition salts and stereochemically isomeric forms thereof are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In a further aspect of this invention, there is provided a method of treating warm-blooded animals, including humans, suffering from, or a method of preventing warm-blooded animals, including humans, to suffer from viral infections, especially HIV infections. Said method comprises the administration, preferably oral administration, of an effective amount of a compound of formula (I), a pharmaceutically acceptable addition salt or a possible stereoisomeric form thereof, to warm-blooded animals, including humans.

In another aspect, the compounds of formula (I) or any subgroup thereof are useful in a method for preventing, treating or combating infection or disease associated with infection of a mammal with a mutant HIV virus, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a multi drug-resistant HIV virus, comprising administering to said mammal an effective amount of a compound of formula (I) or any subgroup thereof.

In yet another aspect, the compounds of formula (I) or any subgroup thereof are useful in a method for inhibiting replication of a HIV virus, in particular a HIV virus having a mutant HIV reverse transcriptase, more in particular a multi-drug resistant mutant HIV reverse transcriptase, comprising administering to a mammal in need thereof an effective amount of a compound of formula (I) or any subgroup thereof.

Preferably, a mammal as mentioned in the methods of this invention is a human being.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets.

Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclo-dextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy-$C_{1-6}$alkyl, particularly hydroxyethyl, hydroxy-propyl or hydroxybutyl; carboxy-$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD). Another type of substituted cyclodextrins is sulfobutylcyclodextrines.

The term mixed ether denotes cyclodextrin derivatives wherein at least two cyclo-dextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "solid dispersion" used hereinafter defines a system in a solid state (as opposed to a liquid or gaseous state) comprising at least two components, in case the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered.

The term "solid dispersion" also comprises dispersions, which are less homogenous throughout than solid solutions. Such dispersions are not chemically and physically uniform throughout or comprise more than one phase, for example, systems having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation. After preparing the solid dispersions, the obtained products can be optionally milled and sieved. The solid dispersion product may be milled or ground to particles having a particle size of less than 600 μm, preferably less than 400 μm and most preferably less than 125 μm. The particles prepared as described hereinabove can then be formulated by conventional techniques into pharmaceutical dosage forms such as tablets and capsules.

The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water-soluble polymer in the preparation of the above-mentioned particles as is disclosed in WO 97/18839. These cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are those described above as agents to aid solubility of the compounds of formula (I).

The ratio of the compound of formula (I) over the water-soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bind to said compound and may be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration. Such beads comprise a central, rounded or spherical core, a coating film of a hydrophilic polymer and a compound of formula (I) and optionally a seal-coating layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), D-D4FC (Reverset™), alovudine (MIV-310), amdoxovir (DAPD), elvucitabine (ACH-126,443), and the like; non-nucleoside reverse transcriptase inhibitors (NNRTIs) such as delarvidine (DLV), efavirenz (EFV), nevirapine (NVP), capravirine (CPV), calanolide A, TMC120, etravirine (TMC125), TMC278, BMS-561390, DPC-083 and the like; nucleotide reverse transcriptase inhibitors (NtRTIs), e.g. tenofovir (TDF) and tenofovir disoproxil fumarate, and the like; compounds of the TIBO (tetrahydroimidazo-[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335; REV inhibitors; protease inhibitors e.g. ritonavir (RTV), saquinavir (SQV), lopinavir (ABT-378 or LPV), indinavir (IDV), amprenavir (VX-478), TMC-126, BMS-232632, VX-175, DMP-323, DMP-450 (Mozenavir), nelfinavir (AG-1343), atazanavir (BMS 232, 632), palinavir, TMC-114, RO033-4649, fosamprenavir (GW433908 or VX-175), P-1946, BMS 186,318, SC-55389a, L-756,423, tipranavir (PNU-140690), BILA 1096 BS, U-140690, and the like; entry inhibitors which comprise fusion inhibitors (e.g. T-20, T-1249), attachment inhibitors and co-receptor inhibitors; the latter comprise the CCR5 antagonists and CXR4 antagonists (e.g. AMD-3100); examples of entry inhibitors are enfuvirtide (ENF), GSK-873,140, PRO-542, SCH-417,690, TNX-355, maraviroc (UK-427,857); a maturation inhibitor for example is PA-457 (Panacos Pharmaceuticals); inhibitors of the viral integrase; ribonucleotide reductase inhibitors (cellular inhibitors), e.g. hydroxyurea and the like.

By administering the compounds of the present invention with other anti-viral agents, which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithio-carbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses, which depend on similar reverse transcriptases for obligatory events in their life cycle.

The pyrimidine derivatives of this invention not only act favorably as regards their capability to inhibit the replication of Human Immunodeficiency Virus (HIV), but also show improved ability to inhibit the replication of mutant strains, in particular strains which show double or multiple mutations in the viral genome encoding for reverse transcriptase. The compounds of this invention therefore may find use in the treatment of patients infected with HIV that has become resistant to one or more known NNRTI drugs (Non Nucleoside Reverse Transcriptase Inhibitor drugs), which strains are referred to as drug or multidrug resistant HIV strains.

The following examples are intended to illustrate the present invention and not to limit its scope thereto.

EXAMPLES

Example 1

To 2.11 g of 4-[(4,6-dichloro-2-pyrimidinyl)amino]benzonitrile (0.00796 mol) was added 500 ml of $CHCl_3$ and the mixture was stirred for 30 minutes to allow the dissolution of almost all of starting compound. 1-bromo-2,5-pyrrolidinedione (0.0397 mol) was added in one portion and the reaction mixture was stirred at room temperature. After about 30 minutes, the mixture became a clear orange solution and the reaction became increasingly reddish with time. After 40 hours, TLC and HPLC/MS showed the reaction was complete. The reaction mixture was purified by flash silica gel column chromatography using CH$_2$Cl$_2$ as eluent. The fractions containing the desired product were isolated and the solvent evaporated. The residue was recrystallized from acetonitrile to afford 1.51 g of 4-[(5-bromo-4,6-dichloro-2-pyrimidinyl)amino]benzonitrile, yield 55% (intermediate 1).

Example 2

A mixture of 0.47 g of 4-hydroxy-3,5-dimethylbenzonitrile (0.00320 mol) and 1,4-dioxane (3 ml) were added to a pressure tube under argon gas. 0.13 g of NaH 60% (0.00320 mol) was added, and the mixture was stirred for 2 minutes. 1-Methyl-2-pyrrolidinone (3 ml) was added and the mixture was stirred for 10 minutes. Intermediate 1 (0.00291 mol) was added and the mixture was heated in a sealed tube at 155° C. for 16 hours. The mixture was poured into water (15 ml). The tube was washed with water, 1,4-dioxane (11 ml) and again with water and the washings were combined with the water phase into which the reaction mixture had been poured. The thus obtained solution was stirred for 15 minutes and placed in the refrigerator. The resulting material was filtered to obtain 1.43 g of 4-[[5-bromo-6-chloro-2-[(4-cyano-phenyl)amino]-4-pyrimidinyl]oxy]-3,5-dimethylbenzonitrile, yield 45% (Intermediate 2).

Example 3

Synthesis of 4-[[6-tetrahydropyranyloxylamino-5-bromo-2-[(4-cyano-phenyl)amino]-4-pyrimidinyl]oxy]-3,5-dimethylbenzonitrile

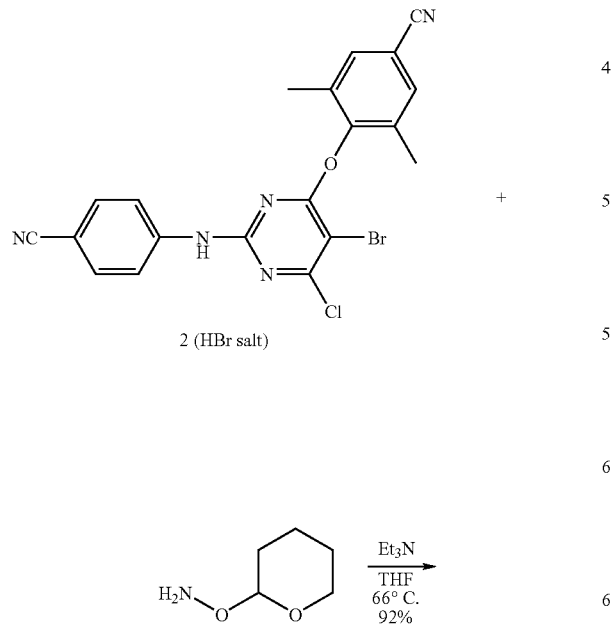

A mixture of the HBr salt of intermediate 2 (1.55 g, 2.89 mmol), obtained as described in example 2, triethylamine (1.43 ml, 1.04 g, 10.2 mmol, 3.5 equiv.) and O-(tetrahydro-2H-pyran-2-yl)hydroxylamine (2.00 g, 17.1 mmol, 5.9 equiv.) was refluxed in THF (30 ml) overnight. LCMS analysis showed 50% conversion. Another batch of O-(tetrahydro-2H-pyran-2-yl)hydroxylamine (1.00 g, 8.54 mmol, 3 equiv.) was added and the reaction mixture was refluxed over the weekend. LCMS analysis showed complete conversion. The reaction mixture was cooled, silica gel was added and the THF was evaporated. Column chromatography using heptane/EtOAc 2/1 containing 0.3% of triethylamine gave 2.7 g of yellow oil, which was taken up in EtOAc, washed twice with sat. NH$_4$Cl, water and brine. After drying with Na$_2$SO$_4$ 1.43 g (92%) of a white yellow foam was obtained (Intermediate 3).

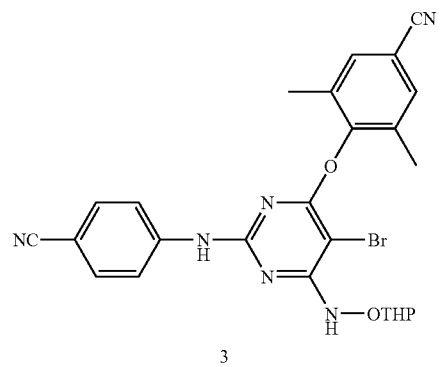

LCMS analysis (4 ml/min linear gradient t$_0$ 100% 10 mM aqueous HCOOH/acetonitrile to t$_{10}$ 100% 10 mM aqueous HCOOH/acetonitrile, UV-DAD): 98% pure, t=7.2 min, mass spectrum m/z 533, 535 [M-H]$^-$.

Example 4

Synthesis of 4-[[6-hydroxylamino-5-bromo-2-[(4-cyanophenyl)amino]-4-pyrimidinyl]oxy]-3,5-dimethylbenzonitrile

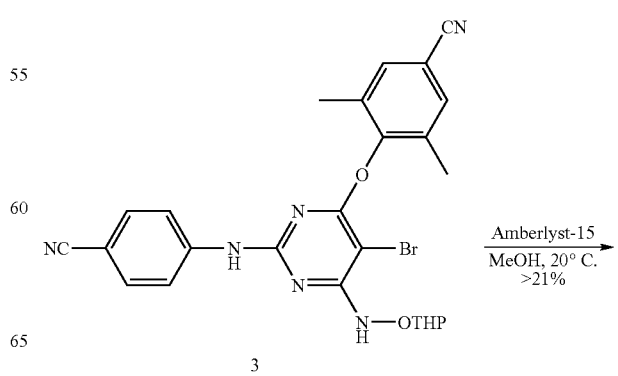

-continued

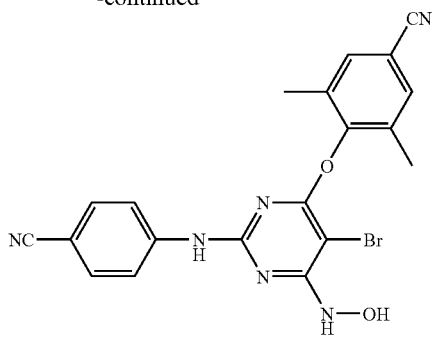

compound 1

A mixture of intermediate 3 (1.40 g, 2.61 mmol) and Amberlyst-15 (1.10 g, 80 wt %) in methanol was stirred overnight at room temperature under argon. The Amberlyst-15 was filtered off and the filtrate was concentrated, taken up in THF, and bound to silica gel. Column chromatography using heptane/EtOAc 1/1 gave only partial separation. The pure fractions were evaporated and the remaining solid was stirred in dichloromethane and filtered to give 250 mg (21%) compound 1 as a white solid. The mixed fractions contained also the desired product, but these were not further purified and analyzed; mp 211° C. (decomposition).

$^1$H NMR (300 MHz, DMSO) δ 2.14 (s, 6H), 7.41 (d, 2H), 7.55 (d, 2H), 7.75 (s, 2H), 9.08 (s, 1H), 9.88 (s, 1H). 9.94 (s, 1H).

LCMS analysis (1 ml/min linear gradient $t_0$ 95% 10 mM aqueous HCOOH/acetonitrile to $t_{15}$ 5% 10 mM aqueous HCOOH/acetonitrile, UV-DAD): 98% pure, t=9.90 min, mass spectrum m/z 449, 451 [M-H]$^-$.

Example 5

Formulations

Capsules

Compound 1, which is the compound described in example 4, is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropyl-methylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-Coated Tablets
Preparation of Tablet Core

A mixture of 100 g of Compound 1, 570 g lactose and 200 g starch are mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10,000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

Example 6

Antiviral Spectrum

Because of the increasing emergence of drug resistant HIV strains, the present compounds were tested for their potency against clinically isolated HIV strains harboring several mutations. These mutations are associated with resistance to reverse transcriptase inhibitors and result in viruses that show various degrees of phenotypic cross-resistance to the currently commercially available drugs such as for instance AZT and delavirdine.

The antiviral activity of the compound of the present invention is evaluated in the presence of wild type HIV and HIV mutants bearing mutations at the reverse transcriptase gene. The activity of the compounds is evaluated using a cellular assay and the residual activity is expressed in $pEC_{50}$ values. The columns IIIB and A-G in the table list the $pEC_{50}$ values against various strains IIIB, A-G.

Strain IIIB is wild type HIV-LAI strain;

Strain A contains mutation Y181C in HIV reverse transcriptase,

Strain B contains mutation K103N in HIV reverse transcriptase,

Strain C contains mutation L100I in HIV reverse transcriptase,

Strain D contains mutation Y188L and S162K in HIV reverse transcriptase,

Strain E contains mutations L100I and K103N in HIV reverse transcriptase,

Strain F contains mutations K101E and K103N in HIV reverse transcriptase.

Strain G contains mutations L100I, K103N, E138G, V179I, Y181C, L214F, V276V/I and A327A/V in HIV reverse transcriptase.

| Compound number | IIIB | A | B | C | D | E | F | G |
|---|---|---|---|---|---|---|---|---|
| 1 | 8.40 | 7.92 | 8.63 | 8.92 | 8.52 | 8.73 | 8.44 | 6.32 |
| A | 8.55 | 8.00 | 8.75 | 8.54 | 8.61 | 8.09 | 8.34 | 5.24 |

Compound A is a compound that has been disclosed in WO00/27825 and has the following structure:

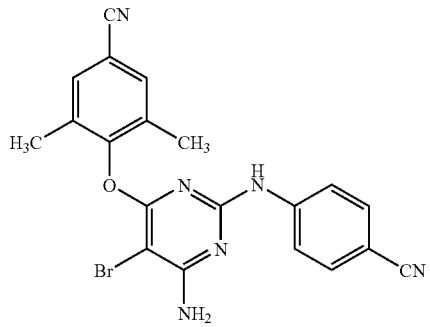

Compared to reference compound A, compound 1 showed improved activity against double mutant strains such as strains E and F. Compound 1 in particular showed improved activity against multiple mutated strain G.

The invention claimed is:
1. A compound of formula

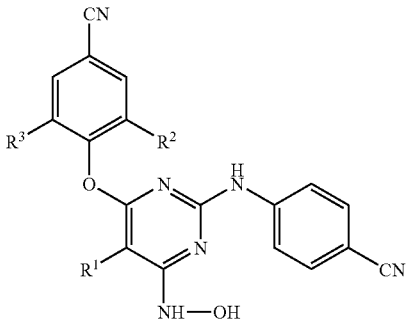

or a pharmaceutically acceptable addition salt thereof, wherein
$R^1$ is bromo;
$R^2$ and $R^3$ are methyl.

* * * * *